United States Patent
Marquais-Bienewald et al.

(10) Patent No.: US 8,697,101 B2
(45) Date of Patent: Apr. 15, 2014

(54) POLYSILOXANE ANTIMICROBIALS

(75) Inventors: Sophie Marquais-Bienewald, Hegenheim (FR); Olof Wallquist, Bottmingen (CH); Andrea Preuss, Basel (CH); Stewart Todd Elder, Butler, NJ (US)

(73) Assignee: BASF SE, Ludwigshafen (DE)

( * ) Notice: Subject to any disclaimer, the term of this patent is extended or adjusted under 35 U.S.C. 154(b) by 796 days.

(21) Appl. No.: 12/309,091

(22) PCT Filed: Jul. 4, 2007

(86) PCT No.: PCT/EP2007/056703
§ 371 (c)(1), (2), (4) Date: Jan. 28, 2011

(87) PCT Pub. No.: WO2008/006744
PCT Pub. Date: Jan. 17, 2008

(65) Prior Publication Data
US 2011/0110998 A1    May 12, 2011

(30) Foreign Application Priority Data
Jul. 14, 2006 (EP) .................................... 06117256

(51) Int. Cl.
*A01N 55/10* (2006.01)
*A01P 1/00* (2006.01)
*C07F 7/08* (2006.01)
*C08G 77/38* (2006.01)
*C08G 77/388* (2006.01)

(52) U.S. Cl.
USPC ........... 424/404; 424/409; 556/437; 556/418; 556/419; 556/424; 544/229; 514/63; 106/18.32

(58) Field of Classification Search
None
See application file for complete search history.

(56) References Cited

U.S. PATENT DOCUMENTS

| | | | |
|---|---|---|---|
| 3,794,736 A | 2/1974 | Abbott et al. | 424/78 |
| 5,013,459 A | 5/1991 | Gettings et al. | 210/764 |
| 5,204,432 A | 4/1993 | Saito et al. | 528/10 |

FOREIGN PATENT DOCUMENTS

| | | | |
|---|---|---|---|
| EP | 0090577 | 10/1983 | |
| FR | 2648676 | 12/1990 | |
| JP | 63-28441 | * 2/1988 | ............... B01J 13/00 |
| JP | 10-330687 | 12/1998 | |
| JP | 2006-257340 | 9/2006 | |
| WO | 95/32977 | 12/1995 | |

OTHER PUBLICATIONS

Huan et al. ("Synthesis and Properties of Polydimethylsiloxane-Containing Block Copolymers via Living Radical Polymerization", Journal of Polymer Science: Part A: Polymer Chemistry, v. 39, 2001, 1833-1842).*
MSDS for Toluene (accessed via. www.sciencelab.com on Mar. 19, 2013, last updated Sep. 6, 2012, pp. 1-6).*
Chem. Abstract 1989:179260 for JP 63028441, Feb. 6, 1988.
Database Registry, Accession No. 735233-59-7, Aug. 29, 2004.
Patent Abstracts of Japan Publication No. 10330687, Dec. 15, 1998.
Chem. Abstract 1991:601111 for FR 2648676, Dec. 28, 1990.
Patent Abstracts of Japan Publication No. 2006257340, Sep. 28, 2006.
G. Sauvet et al., Journal of Applied Polymer Science, vol. 75, pp. 1005-1012, (2000).

* cited by examiner

*Primary Examiner* — Kortney L Klinkel
(74) *Attorney, Agent, or Firm* — Shiela A. Loggins

(57) ABSTRACT

Disclosed are oligo- or polysiloxanes, which are characterized by containing at least 3, for example 4-3000, Si atoms in the main chain, and wherein at least one thereof is contained in a moiety of the formula (I) whose variables and attachments are described within.

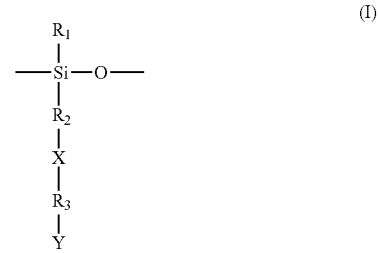

The disclosed are oligo- or polysiloxane compounds are effective as antimicrobials.

15 Claims, No Drawings

POLYSILOXANE ANTIMICROBIALS

The present application pertains to a material having antimicrobial properties by containing a specific oligo- or polysiloxane antimicrobial, to a corresponding use and a process for the production of such a material, and to the novel antimicrobial compounds.

Antimicrobials are often based on quaternary ammonium compounds. In order to improve the properties of such compounds such as efficient and long lasting antimicrobial action, compatibility with the substrate, good persistency on or in the substrate, low toxicity, a number of modifications have been proposed including the introduction of a silyl group. WO 95/32977 teaches the use of a trisiloxane containing a quaternary ammonium group linked to the central silicon atom by an ether bridge, and an oligosiloxane containing quaternary ammonium end groups, as an antimicrobial agent. Sauvet et al., J. Appl. Pol. Sc. 75, 1005 (2000) disclose a similar polysiloxane for the same purpose.

In view of the ability of microorganisms to adapt to a variety of adverse circumstances including the development of resistance, novel methods and materials are required for the treatment of surfaces, materials and/or products, e.g. by classes of compounds that allow to inhibit microbial growth or even show microbicidal activity against a broad range of microorganisms, e.g. one or more microorganisms selected from bacteria, fungi, yeasts and algae, and/or even have negative influence on the settlement of multicellular organisms, such as algae, mosses or ferns, on and/or in materials or objects and thus are useful inter alia for applications in preservation, as additives in plastics, in coatings, on textiles, in paper, in cosmetics, in pharmaceutical formulations or corresponding containers, in home or personal care applications and the like, be it with natural and/or with synthetic materials, and for other corresponding uses. The same time, there is a growing need for effective antimicrobials which show low toxicity on mammals.

It has now been found, that certain oligo- or polysiloxanes show especially advantageous properties in this regard as antimicrobial agents. Present invention therefore pertains to a material containing a certain oligo- or polysiloxane, either as a bulk additive or on its surface after treatment of its surface with said oligo- or polysiloxane, or in both forms, wherein the oligo- or polysiloxane is characterized by containing at least 3, for example 4-3000, Si atoms in the main chain, and wherein at least one thereof is contained in a moiety of the formula I

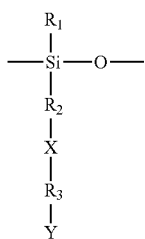
(I)

whose open bond of the O atom is linked to another Si atom of the oligo- or polysiloxane main chain, and whose open bond of the Si atom is linked either to another O atom of the oligo- or polysiloxane main chain or to $R'_1$, where $R_1$ and $R'_1$ independently are $C_1$-$C_{10}$alkyl,
$R_2$ and $R_3$ independently are $C_1$-$C_{18}$alkylene,
X is a divalent spacer group selected from O, $NR_4$, $N(COR'_5)$, $CONR'_4$, $OCONR'_4$;
Y is selected from $OCOR_5$, $NHCOR_5$, $NHR_4$, $COOR_5$, $CONHR_4$, $NR'_4R_4$;
$R_4$ is selected from $C_6$-$C_{18}$ organic residues containing at least one aryl moiety;
$R'_4$ is as defined for $R_4$; or is selected from H, $C_1$-$C_{20}$alkyl, $C_7$-$C_{20}$phenylalkyl, $C_4$-$C_{12}$cycloalkyl;
$R_5$ is $R_7$—Z;
$R'_5$ is as defined for $R_5$; or is selected from H, $C_1$-$C_{20}$alkyl, $C_7$-$C_{20}$phenylalkyl, $C_4$-$C_{12}$cycloalkyl;
$R_7$ is $C_1$-$C_{20}$alkylene, which may be interrupted by phenylene, $C_4$-$C_{12}$cycloalkylene, O, $NR'_4$;
or is unsubstituted or substituted phenylene or $C_4$-$C_{12}$cycloalkylene;
Z is halogen or $N^+R_8R_9R_{10}$;
$R_8$, $R_9$ and $R_{10}$ independently are selected from $C_1$-$C_{20}$alkyl, $C_7$-$C_{20}$phenylalkyl, $C_4$-$C_{12}$cycloalkyl, unsubstituted or substituted aryl; or 2 of $R_8$, $R_9$ and $R_{10}$ are linked together to form a quaternized aliphatic, substituted or unsubstituted N-heterocyclic ring of 4-6 carbon atoms such as a piperidine ring; or all of $R_8$, $R_9$ and $R_{10}$ are linked together to form, together with the nitrogen atom they are bonding to, a substituted or unsubstituted N-heterocyclic ring system of 4-7 carbon atoms, preferably an aromatic ring such as a pyridine ring

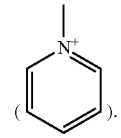

The present compounds combine antimicrobial, preservative and microorganism adhesion and biofilm inhibiting effect for the protection of the article and/or material, especially a broad (direct) antimicrobial effect.

Any positive charge in the present compounds is neutralized by the equivalent number of cosmetically or pharmaceutically acceptable anions, selected e.g. from halogenide anions, especially chloride or bromide; sulfuric or sulfonic, carboxylic anions such as acetic or benzoic; the compound containing one or more charged group(s) thus are in the form of a salt.

An anion or anions (counterion(s)) leading to charge neutralisation), where present, form a corresponding substantially neutral salt of an ammonium compound of the formulae I, II—this means preferably that a number of anions is present that substantially leads to charge neutralization. However, e.g. on surfaces, it may also be possible that counterions are stripped away so that a net charge may result at least temporarily—this is for example intended to be meant by the term "substantially leads to charge neutralization".

The compounds may be used directly as antimicrobials, or may be used in modified form (e.g. as another salt, or in substituted, etherified, esterified, or quaternized form).

In the context of the definitions given, any alkyl is, for example, branched or unbranched alkyl such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl.

Aryl moieties are preferably selected from $C_4$-$C_{10}$aryl such as phenyl, naphthyl, pyridyl, pyrimidyl, pyridylium, pyrimidylium, triazinyl, each of which may be unsubstituted or substituted.

$C_6$-$C_{18}$ organic residues containing at least one aryl moiety mainly are selected from aryl moieties or alkyl moieties substituted by aryl or interrupted by arylene; examples include benzyl, xylylethyl, phenyl-pydimidyl, methylpydimidyl, phenyl-methyl-pydimidyl.

Arylene is a divalent residue derived from the corresponding monovalent aryl by abstraction of one hydrogen atom.

Halogen is mainly fluoro, chloro, bromo or iodo, especially bromo or chloro.

Cycloalkyl comprises for example cyclopentyl, cyclohexyl, cycloheptyl, cyclooctyl, cyclononyl, cyclodecyl, cycloundecyl and cyclododecyl, with main emphasis to cyclopentyl, cyclohexyl, cyclododecyl; especially cyclohexyl.

$C_7$-$C_{20}$Phenylalkyl stands for an alkyl residue substituted by phenyl; typical examples are benzyl, phenylethyl, cumyl, phenylbutyl.

Alkylene or cycloalkylene are divalent residues derived from the corresponding monovalent alkyl or cycloalkyl by abstraction of one hydrogen atom in any position, thus including alkylidene or cycloalkylidene, respectively.

Alkylene, which may be interrupted or end-capped by phenyl or $C_4$-$C_{12}$cycloalkylene, O, $NR'_4$; or is unsubstituted or substituted phenylene or $C_4$-$C_{12}$cycloalkylene;

Thus, examples for $R_4$ are phenyl, naphthyl, pyridyl, pyrimidyl, pyridylium, pyrimidylium, triazinyl; or $C_1$-$C_8$alkyl substituted by phenyl (such as benzyl), naphthyl, pyridyl, pyrimidyl, pyridylium, pyrimidylium, triazinyl; where each of phenyl, naphthyl, pyridyl, pyrimidyl, pyridylium, pyrimidylium, triazinyl optionally may be substituted. An example is an $C_1$-$C_8$alkyl and/or phenyl substituted pyrimidyl such as 2-phenyl-4-methylpydimid-6-yl

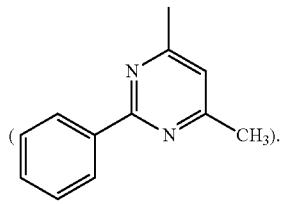

Substituents usually are selected from $C_1$-$C_8$alkyl, halogen, amino, phenyl, $C_1$-$C_4$alkylphenyl, benzyl.

$R_1$ or $R'_1$ often is a short chain alkyl such as $C_1$-$C_4$alkyl, especially methyl.

Thus, the new class of oligo- or polysiloxane compounds with high bactericidal and fungicidal activity often complies with the formula II

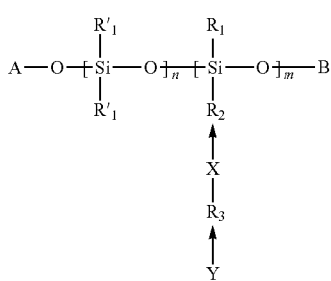

(II)

wherein m is selected from the range 1-1000, and n is selected from the range 0-1000; $R_1$, $R'_1$, $R_2$, $R_3$, X and Y are as defined above, and A and B independently are groups of the formula —Si($R_{11}R_{12}R_{13}$), wherein each of $R_{11}$, $R_{12}$, $R_{13}$ independently is as defined for $R_1$, or A and B, especially in oligomeric compounds wherein the sum n+m is from the range 4-20, together may form a direct bond. Where A and B together are a direct bond, the resulting compound of the formula II is cyclic.

Units of the formula —Si($R'_1$)$_2$—O— (IIa) and/or —Si($R_1$)($R_2XR_3Y$)—O— (IIb) in the present compounds may be arranged randomly or in blocks.

The index n is preferably from the range 2-500, especially 3-300; The index m is preferably from the range 1-1000, more preferably from the range 2-500, especially 3-300.

The present oligo- or polysiloxanes are novel compounds; they are preferably open-chain compounds. With particular preference, A and B are trialkylsilyl, especially trimethylsilyl.

Of emphasized importance are compounds of the formula I or II, wherein $R_1$ and $R'_1$ independently are $C_1$-$C_4$alkyl, $R_2$ and $R_3$ independently are $C_2$-$C_{12}$alkylene, X is a divalent spacer group selected from O, $NR_4$, $N(COR_5)$;

Y is selected from $OCOR_5$, $NHCOR_5$, $COOR_5$, $CONHR_4$, $NR'_4R_4$;

$R_4$ is selected from $C_4$-$C_{10}$aryl moieties or $C_1$-$C_{12}$alkyl moieties substituted by $C_4$-$C_{10}$aryl or $C_2$-$C_{12}$alkyl interrupted by $C_4$-$C_{10}$arylene, wherein each aryl or arylene may be unsubstituted or substituted;

$R'_4$ is as defined for $R_4$; or is selected from H, $C_1$-$C_{20}$alkyl, $C_4$-$C_{12}$cycloalkyl;

$R_5$ is $R_7$—Z;

$R_7$ is $C_2$-$C_{20}$alkylene, which may be interrupted by phenyl or $C_4$-$C_{12}$cycloalkylene, O, $NR'_4$; or is unsubstituted or substituted phenylene or $C_4$-$C_{12}$cycloalkylene;

Z is halogen or $N^+R_8R_9R_{10}$;

$R_8$, $R_9$ and $R_{10}$ independently are selected from $C_1$-$C_{20}$alkyl, $C_7$-$C_{20}$phenylalkyl, $C_4$-$C_{12}$cycloalkyl, unsubstituted or substituted aryl; or 2 of $R_8$, $R_9$ and $R_{10}$ are linked together to form a quaternized aliphatic, substituted or unsubstituted N-heterocyclic ring of 4-6 carbon atoms such as a piperidine ring; or all of $R_8$, $R_9$ and $R_{10}$ are linked together to form, together with the nitrogen atom they are bonding to, a substituted or unsubstituted N-heterocyclic ring system of 4-7 carbon atoms, especially those wherein $R_4$ is selected from phenyl, naphthyl, pyridyl, pyrimidyl, pyridylium, pyrimidylium, triazinyl; or $C_1$-$C_8$alkyl substituted by phenyl, naphthyl, pyridyl, pyrimidyl, pyridylium, pyrimidylium, triazinyl; or phenyl, naphthyl, pyridyl, pyridylium, pyrimidylium, triazinyl, each of which is substituted by $C_1$-$C_8$alkyl, halogen, amino, phenyl, $C_1$-$C_4$alkylphenyl, benzyl; or $C_1$-$C_8$alkyl, which is substituted by phenyl, naphthyl, pyridyl, pyrimidyl, pyridylium, pyrimidylium, triazinyl, each aromatic core being substituted by $C_1$-$C_8$alkyl, halogen, amino, phenyl, $C_1$-$C_4$alkylphenyl, benzyl;

$R'_4$ is as defined for $R_4$; or is H;

$R_7$ is $C_2$-$C_{20}$alkylene;

Z is halogen or $N^+R_8R_9R_{10}$;

$R_8$, $R_9$ and $R_{10}$ independently are selected from $C_1$-$C_{20}$alkyl, $C_7$-$C_{20}$phenylalkyl, $C_4$-$C_{12}$cycloalkyl; or all of $R_8$, $R_9$ and $R_{10}$ are linked together to form, together with the nitrogen atom they are bonding to, a substituted or unsubstituted N-heterocyclic ring system of 4-7 carbon atoms.

Compounds wherein Z is halogen are especially important as intermediates for preparing quaternized compounds, wherein Z is $N^+R_8R_9R_{10}$. An especially valuable group of compounds of the formula I or II for use as antimicrobial agent is defined by X being O or N(COR$_5$) and Y is OCOR$_5$ or NHCOR$_5$, where R$_7$ is C$_6$-C$_{18}$alkylene; Z is N$^+$R$_8$R$_9$R$_{10}$; R$_8$, R$_9$ are independently selected from C$_1$-C$_4$alkyl such as methyl; and R$_{10}$ is selected from C$_2$-C$_{18}$alkyl, C$_7$-C$_{20}$phenylalkyl, C$_5$-C$_{12}$cycloalkyl; or all of R$_8$, R$_9$ and R$_{10}$ are linked together to form, together with the nitrogen atom to form an N-heterocyclic aromatic ring of 4-7 carbon atoms; or by X being NR$_4$ and Y being NHR$_4$, where R$_4$ is phenyl, pyridyl, pyrimidyl, triazinyl; or C$_1$-C$_4$alkyl substituted by phenyl, pyridyl, pyrimidyl, triazinyl; or is phenyl, pyridyl, pyrimidyl, triazinyl, each of which is substituted by C$_1$-C$_4$alkyl, halogen, phenyl, C$_1$-C$_4$alkylphenyl, benzyl; or is C$_1$-C$_4$alkyl, which is substituted by phenyl, pyridyl, pyrimidyl, triazinyl, each aromatic core being substituted by C$_1$-C$_4$alkyl, halogen, phenyl, C$_1$-C$_4$alkylphenyl, benzyl;

and most especially is defined by X being O or N(COR$_5$) and Y is OCOR$_5$ or NHCOR$_5$, where R$_7$ is C$_8$-C$_{14}$alkylene; Z is N$^+$R$_8$R$_9$R$_{10}$, where R$_8$, R$_9$ independently are selected from C$_1$-C$_4$alkyl such as methyl and R$_{10}$ is selected from C$_8$-C$_{14}$alkyl, C$_7$-C$_{14}$phenylalkyl, cyclohexyl; or all of R$_8$, R$_9$ and R$_{10}$ are linked together to form a group of the formula

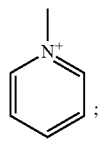

or by X being NR$_4$ and Y being NHR$_4$, where R$_4$ is phenyl, pyrimidyl; or C$_1$-C$_4$alkyl substituted by phenyl, pyrimidyl; or is phenyl or pyrimidyl, each of which is substituted by C$_1$-C$_4$alkyl and/or phenyl.

The present compounds may conveniently be prepared using suitably functionalized oligo- or polysiloxanes as educts, such as products containing one or more functional groups selected from hydroxy, amino, carboxy, ester, halogeno, oxiranyl etc. A wide variety of these products is known in the art, many products are commercially available. The present compounds may, for example, be prepared starting from an oligo- or polysiloxane containing one or more moieties of the formula

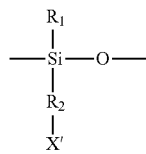

where chain length, optional further repeating units, end groups, and the residues R$_1$, R$_2$ are as defined above. The reactive moiety X' may be selected, for example, from leaving groups or suitable moieties containing such a leaving group such as chloro, bromo, anhydride, acyl halogenide, or may be a suitable nucleophil such as OH, NHR'$_4$. This may be reacted with a reagent of the formula X"—R$_3$—Y or X"—R$_3$—Y' wherein X" is a suitable reaction partner for group X' forming the linkage X, R$_3$ and Y are as defined above, and Y' is a precursor to group Y which may be converted into Y in a subsequent reaction step, e.g. for conversion of Y' into a quaternized nitrogen (ammonium) moiety.

Reactions may be carried out, for example, using suitable bifunctional reagents X"—R$_3$—Y or X"—R$_3$—Y', wherein X" has a higher reactivity towards X' than Y or Y'. Reactions and reagents of this type are widely known in the art, examples are given further below. Examples for functional groups suitable to achieve the present condensation/substitution reaction include, but are not limited to, acid anhydride, acyl chlorides, suitable halogenides, alcohol or amino functions, oxiranes.

Conditions for the reaction and work-up conveniently are chosen in accordance or anology to methods known in the art, especially with respect to reaction temperatures (e.g. between room temperature and boiling point of the solvent or reagent, or between 0 and about 150° C.), pressure (usually at atmospheric pressure, suitably between 0 and about 10 bar), oxygen exclusion (using a suitable inert gas such as nitrogen or argon, especially in cases where high reaction temperatures and/or oxygen sensitive educts/reagents are used), solvent (e.g. inert solvents such as hydrocarbons of suitable boiling range, chlorinated or further substituted hydrocarbons, non-reactive mono-, oligo- or polysiloxanes; or none, especially in case that educt or reagent, e.g. an excess thereof, may be used as a solvent), reaction time (e.g. between 0.5 and 24 hours), isolation and purification (using common steps such as washing, extraction, precipitation, filtration, evaporation/removal of solvent or remaining educt/reagent, etc.).

The invention thus relates to compositions comprising one or more of the compounds mentioned in the preceding paragraph (also sometimes termed "compositions of the invention" hereinafter, implying also the use of such compositions according to the invention) which are appropriate especially for application to materials and articles, e.g. for covering materials or articles, for addition to materials or articles, e.g. by being admixed to materials during their manufacture, and/or for impregnating materials or articles, where said compositions may comprise a compound of the invention and may, in addition, comprise other additives or carrier materials, such as binders, solvents, buffers or the like.

Among the compositions of interest, there may especially be mentioned, antimicrobial compositions, antifouling compositions, coating compositions or materials (coatings), paints, coating systems, cosmetic formulations (including oral preparations and deodorants), home care compositions, pharmaceutical compositions (including oral preparations), antimicrobial preparations, laundry detergent and/or fabric care compositions, a fabric, a fibre, a non-woven, a molded or blow-molded article, a film, each independently forming a preferred embodiment and preferably defined as below.

In a further embodiment, the invention relates to the use of one or more compounds or compositions according to the invention as defined above or preferably below in order to achieve an antimicrobial, preservative and/or microorganism adhesion inhibiting effect for the protection of one or more articles and/or materials, said use especially comprising adding one or more of said compounds or a composition comprising one or more of said compounds to said article(s) and/or material(s), especially for use as antimicrobial. The addition may be by integration into the material (e.g. by admixing during manufacture of a product, such as an article or a material), by impregnation of an article or material and/or by application to a surface e.g. of an article or material.

Yet a further embodiment of the invention relates to a process of manufacture of one or more of the novel compounds of the invention as defined above, and/or to a process of manufacture of a novel composition comprising one or more compounds according to the invention.

Compounds of the invention may be converted into salts, or salts thereof into different salts, by adding or replacing, respectively, anions thereto/therein by (other) anions according to customary methods, e.g. by precipitation in the presence of metal or ammonium salts with the desired anions or using anion exchangers.

The preparation of compositions according to the invention comprises admixing one or more of the present oligo- or polysiloxane compounds, or salts thereof, with one or more other additives, e.g. those mentioned below. Compounds, compound mixtures or compositions comprising of the invention are also referred to as "antimicrobial agents" hereinafter.

Where the term "comprising" is used, this is intended to mean that the component, components, feature or features mentioned or enumerated thereafter may be fulfilled not only alone, but that also one or more other components and/or features (e.g. other additives, other actions) may be present in addition to those specifically mentioned. This is in contrast to the term "containing" or "consisting of" which mean that no other components or features are included except for those specifically mentioned after such an expression and thus denote a complete enumeration/representation of features and/or components. Wherever "comprising" is used, this may (independently of other occurrences) be replaced by the narrower term "consisting of" or (in case of processes or methods) by "containing the step of", where possible and expedient, thus leading to specific and preferred embodiments of the invention.

"About" wherever used in the present disclosure means that a certain deviation from a numerical value may be present and the corresponding value is not intended to mean an absolute boarder as will be apparent to a person skilled in the art; it preferably means "±20%" of the respective numerical value, more preferably "±10%", yet more preferably "±5%" thereof, and most preferably can be deleted so that only the respective numerical value remains without preceding "about".

Antimicrobial activity means an at least partially microorganism inactivating (viability affecting), especially antibiotic or microbicidal (microorganism impeding or especially killing) activity that leads to a direct partial or complete inhibiting effect on microorganisms, such as especially bacterial, protozoic, fungal and/or algal cells or multicellular microorganisms, especially antibacterial or antifungal properties, especially against those microorganisms mentioned in the Examples, or in a broader sense also to inhibiting effects on virus or phages. The effect is especially on the basis of a negative effect on the metabolism, structure or reproduction (e.g. cell division or steps preceding it) of the microorganism(s), e.g. a toxic effect.

Preservative activity means especially that articles (goods in any form) and/or materials are preserved against a decomposing activity, especially by decomposition of one or more of its structural components due to microorganism attack on structural components of articles or materials. For example, in the case of pharmaceutical compositions or food preservative activity especially means that the structure of an active chemical entity or important food constituents such as vitamins are preserved against decomposition by microorganisms.

Microorganism adhesion inhibiting activity means especially that the colonization of an article or material by microbes is diminished or completely abolished due to mainly purely structural effects such as the provision of a surface structure that impedes the binding of microorganisms or other materials that allow for the anchoring of microorganisms. Thus the basis is not an effect on the viability of the microorganism but an effect on the ability of the microorganism to physically settle on or in a material or article.

Apply, application of, addition of or add(ing) and the like especially means to coat, impregnate or mix with.

Bulk addition especially refers to the addition to a material by admixing an compound, compound mixture or a composition comprising a compound or compound mixture comprising one or more compounds of the formula I and/or II to the material of the article or material, during its manufacture (e.g. by admixing to starting materials, e.g. granules, powders, solutions or the like), in contrast to coating or impregnation which correspond to application on an already manufactured material or article. It also comprises addition to powders such as materials for pharmaceuticals.

In principle, the compounds etc. of the formula I, II may be applied by integration, admixing, impregnation, impregnating and/or coating includes homogenous integration or admixing, inhomogenous integration or admixing, complete or partial impregnation and/or complete or partial coating.

Compositions according to the invention, which can also be called antimicrobial compositions hereinafter, may, in addition to a compound of the formula I, II, which may also be present as sole component, comprise one or more other additives such as a binder, solvents and the like. The invention also comprises the use of a compound according to the invention or such a composition, a mixture of such compounds or a composition comprising these.

The present invention also relates to antimicrobial compositions or their use to achieve antimicrobial (especially preferred), preservation and/or microorganism adhesion inhibiting effects, comprising a carrier, especially an organic carrier material, (component (A)) and a compound or compound mixture according to the invention (component (B)).

Suitable carriers for making use of the present antimicrobial compounds may be selected from solid inorganic carriers (such as natural or synthetic ceramics, metals), aqueous liquid or semisolid carriers (e.g. cosmetic preparations including o/w dispersions or emulsions, process water, laundry liquors, home or fabric care formulations, antimicrobial formulations, paint formulations), organic liquid or semisolid carriers (e.g. cosmetic preparations including w/o dispersions or emulsions, antimicrobial formulations, paint formulations), solid organic carriers (including plastics, rubbers, molded articles, blow molded articles, films, fibers, fabrics, non-wovens).

Of special interest are also compositions wherein the composition is a coating composition and component (a) is an organic film-forming binder.

Of special interest are transparent coating compositions which after curing lead to transparent coatings.

The composition, e.g. coating, may be solvent borne or aqueous. Aqueous compositions are typically considered more environmentally friendly. The coating or other composition according to the invention is, for example, aqueous dispersion of a compound according to the invention and a binder or a water based coating or paint. The coating composition is preferably a coating material or paint, especially an aqueous coating material or an aqueous paint.

The antimicrobial compositions of present invention are for example used as a coating applied to a surface which is exposed to conditions favorable for bioaccumulation.

The antimicrobial composition of the present invention may be part of a complete coating or paint formulation, such as a marine gel-coat, shellac, varnish, lacquer or paint, or the anti microbial composition may comprise only a compound (or mixture) of the invention and binder, or a compound (or mixture) of the invention, binder and one or more additives. It is anticipated that other additives encountered in such coating formulations or applications will find optional use in the present applications as well.

Examples of coating materials are lacquers, paints or varnishes. These always contain an organic film-forming binder in addition to other, optional components.

Preferred organic film-forming binders are epoxy resins, polyurethane resins, amino resins, acrylic resins, acrylic copolymer resins, polyvinyl resins, phenolic resins, styrene/butadiene copolymer resins, vinyl/acrylic copolymer resins, polyester resins, UV-curable resins or alkyd resins, or a mixture of two or more of these resins, or an aqueous basic or acidic dispersion of these resins or mixtures of these resins, or an aqueous emulsion of these resins or mixtures of these resins.

Biocompatible coating polymers, such as poly[alkoxyalkanoate-co-3-hydroxyalkenoate (PHAE) polyesters (see e.g. Geiger et al., Polymer Bulletin 52, 65-70 (2004), can also serve as binders in the present invention.

Of particular interest are organic film-forming binders for aqueous coating compositions, e.g. alkyd resins; and hybrid systems based on, for example, epoxy acrylates.

Further coating materials, binder systems, methods of incorporation for the present compounds are as described in copending patent application EP06114888.8 or in WO04106311 (corresponding to the use of the stabilizer component (B) described in the latter document; see especially passage ranging from bottom paragraph of page 70 until paragraph 3 on page 79).

Preferably, component (B) is contained in the carrier in an amount from 0.01 to about 40%; preferred amounts added to the organic material range from 0.01 to 20%, in particular 0.01 to 10%, for example 0.01 to 5%, relative to the weight of the carrier or organic material.

Coating systems include marine coatings, wood coatings, other coatings for metals and coatings over plastics and ceramics. Exemplary of marine coatings are gel coats comprising an unsaturated polyester, a styrene and a catalyst.

The coating is, for example a house paint, or other decorative or protective paint. It may be a paint or other coating that is applied to cement, concrete or other masonry article. The coating may be a water proofer as for a basement or foundation.

As the antimicrobial composition is intended for use in maritime applications as well as near pool areas etc., the composition may be part of a non-skid coating including coatings for stairs, paths and handrails.

The coating composition is applied to a surface by any conventional means including spin coating, dip coating, spray coating, draw down, or by brush, roller or other applicator. A drying or curing period will typically be needed. For impregnating, it is also possible to use pressure impregnation or impregnation without pressure application.

The antimicrobial composition may be part of a polish, such a furniture polish, or a dispersant or surfactant formulation such as a glycol or mineral oil dispersion or other formulation as used in for example wood protection, paper or cardboard protection or the like.

Examples of useful surfactants include, but are not limited to, polyoxyethylene-based surface-active substances, including polyoxyethylene sorbitan tetraoleate (PST), polyoxyethylene sorbitol hexaoleate (PSH), polyoxyethylene 6 tridecyl ether, polyoxyethylene 12 tridecyl ether, polyoxyethylene 18 tridecyl ether, Tween® surfactants, Triton® surfactants, and the polyoxyethylene-polyoxypropylene copolymers such as the Pluronic® and Poloxamer® product series (from BASF). Other matrix-forming components include dextrans, linear PEG molecules (MW 500 to 5,000,000), star-shaped PEG molecules, comb-shaped and dendrimeric, hyperbranched PEG molecules, as well as the analogous linear, star, and dendrimer polyamine polymers, and various carbonated, perfluorinated (e.g., DuPont Zonyl® fluorosurfactants) and siliconated (e.g, dimethylsiloxane-ethylene oxide block copolymers) surfactants (other than those of the present invention).

Given the wide array of applications for the present antimicrobial compositions, the composition may contain one or more other additives such as antioxidants, UV absorbers, benzofuran-2-ones, polyamide stabilizers, metal stearates, nucleating agents, fillers, reinforcing agents, clarifiers, modifiers, acid scavengers, lubricants, emulsifiers, dyes, pigments, dispersants, surfactants, optical brighteners, flow control agents, flame retardants, antistatic agents, blowing agents, thixotropic agents, adhesion promoters, light stabilizers, curing catalysts, accelerators, inhibitors and the like, such as the materials listed below, or mixtures thereof:

1. Antioxidants
  1.1. Alkylated monophenols, for example 2,6-di-tert-butyl-4-methylphenol
  1.2. Alkylthiomethylphenols, for example 2,4-dioctylthiomethyl-6-tert-butylphenol
  1.3. Hydroquinones and alkylated hydroquinones, for example 2,6-di-tert-butyl-4-methoxyphenol, 2,5-di-tert-butylhydroquinone,
  1.4. Tocopherols, for example α-tocopherol
  1.5. Hydroxylated thiodiphenyl ethers, for example 2,2'-thiobis(6-tert-butyl-4-methylphenol),
  1.6. Alkylidenebisphenols, for example 2,2'-methylenebis(6-tert-butyl-4-methylphenol),
  1.7. O-, N- and S-benzyl compounds, for example 3,5,3',5'-tetra-tert-butyl-4,4'-dihydroxydibenzyl ether
  1.8. Hydroxybenzylated malonates, for example dioctadecyl-2,2-bis(3,5-di-tert-butyl-2-hydroxybenzyl)malonate,
  1.9. Aromatic hydroxybenzyl compounds, for example 1,3,5-tris(3,5-di-tert-butyl-4-hydroxybenzyl)-2,4,6-trimethylbenzene,
  1.10. Triazine compounds, for example 2,4-bis(octylmercapto)-6-(3,5-di-tert-butyl-4-hydroxyanilino)-1,3,5-triazine,
  1.11. Benzylphosphonates), for example dimethyl-2,5-di-tert-butyl-4-hydroxybenzylphosphonate
  1.12. Acylaminophenols, for example 4-hydroxylauranilide
  1.13. Esters of β-(3,5-di-tert-butyl-4-hydroxyphenyl)propionic acid with mono- or polyhydric alcohols
  1.14. Esters of β-(5-tert-butyl-4-hydroxy-3-methylphenyl) propionic acid with mono- or polyhydric alcohols
  1.15. Esters of β-(3,5-dicyclohexyl-4-hydroxyphenyl)propionic acid with mono- or polyhydric alcohols,
  1.16. Esters of 3,5-di-tert-butyl-4-hydroxyphenyl acetic acid with mono- or polyhydric alcohols
  1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide
  1.18. Ascorbic acid (vitamin C)
  1.19. Aminic antioxidants, for example N,N'-di-isopropyl-p-phenylenediamine 2. UV absorbers and light stabilizers
  2.1. 2-(2'-Hydroxyphenyl)benzotriazoles, for example 2-(2'-hydroxy-5'-methylphenyl)-benzotriazole
  2.2. 2-Hydroxybenzophenones, for example the 4-hydroxy derivatives.
  2.3. Esters of substituted and unsubstituted benzoic acids, for example 4-tert-butyl-phenyl salicylate
  2.4. Acrylates, for example ethyl α-cyano-β,β-diphenylacrylate 2.5. Nickel compounds, for example nickel complexes of 2,2'-thio-bis[4-(1,1,3,3-tetramethylbutyl)phenol]

2.6. Sterically hindered amines, for example bis(2,2,6,6-tetramethyl-4-piperidyl)sebacate, 2.7. Oxamides, for example 4,4'-dioctyloxyoxanilide 2.8. 2-(2-Hydroxyphenyl)-1,3,5-triazines, for example 2,4,6-tris(2-hydroxy-4-octyloxyphenyl)-1,3,5-triazine 3. Metal deactivators, for example N,N'-diphenyloxamide, 4. Phosphites and phosphonites, for example triphenyl phosphite 5. Hydroxylamines, for example N,N-dibenzylhydroxylamine 6. Nitrones, for example, N-benzyl-alpha-phenylnitrone 7. Thiosynergists, for example dilauryl thiodipropionate, 8. Peroxide scavengers, for example esters of β-thiodipropionic acid 9. Polyamide stabilizers, for example copper salts in combination with iodides and/or phosphorus compounds and salts of divalent manganese.

10. Basic co-stabilizers, for example melamine

11. Nucleating agents, for example inorganic substances, such as talcum, metal oxides, 12. Fillers and reinforcing agents, for example calcium carbonate, silicates 13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384; (see also list on pages 55-65 of WO04106311, which is hereby incorporated by reference). The additional additives, especially stabilizers, are added, for example, in concentrations of 0.01 to 10%, for example 0.2-5%, relative to the total weight of the material or article. Certain additives, such as fillers, flame retardants etc. may also be used in higher loadings, e.g. up to 50%, especially up to 30% by weight of the organic polymer matrix.

Incorporation of component (B) and, if desired, further additives into the "bulk" polymeric, organic material is carried out by known methods, for example before or during moulding or else by applying the dissolved or dispersed compounds to the polymeric, organic material, if appropriate with subsequent slow evaporation of the solvent. Component (B) can also be added to the materials in the form of a masterbatch or a colloidal sol or organosol containing for example 5 to 50% by weight of component (B).

A preferred class of organic carrier materials are polymers, like those given in WO04106311 (see below), in particular synthetic polymers, for example thermoplastic polymers. Polyamides, polyurethanes and polyolefins are particularly preferred. Examples of preferred polyolefins are polypropylene or polyethylene.

Component (B) can also be added before or during polymerisation or before crosslinking.

Component (B) can be incorporated into the material in pure form or encapsulated in waxes, oils or polymers.

Component (B) can also be sprayed or applied as powder onto the material.

The materials thus treated as mentioned above can be used in various forms, for example as films, fibers, ribbons, molded materials, profiles, coatings or as binders for paints, adhesives or cement.

The antimicrobial (e.g. antifouling) composition of the invention may be a coating or a film, a composition for admixing to a material and/or a composition for impregnating a material and/or a product. When the antimicrobial composition is a thermoplastic film which is applied to a surface, for example, by the use of an adhesive or by melt applications including calendaring and co-extrusion, the binder is the thermoplastic polymer matrix used to prepare the film.

When the antimicrobial composition is, e.g., a coating, it may be applied as a liquid solution or suspension, a paste, gel, oil or the coating composition may be a solid, for example a powder coating which is subsequently cured by heat, UV light or other method. As the antimicrobial composition of the invention may be a coating or a film, the binder can be comprised of any polymer used in coating formulations or film preparation.

Further methods of incorporation of the present compounds include those described in the passage from page 66, bottom paragraph, until and including page 69, paragraph 2, of WO04106311 for the UV filters presented therein. This passage is hereby incorporated by reference.

Examples of materials to which a compound or mixture of compounds or composition comprising such a compound or mixture can be applied as a coating or in bulk are especially organic materials, preferably synthetic materials, preferably made from polymers (which may also be used in forming articles comprising them or especially consisting of them), such as thermoplastic, elastomeric, inherently crosslinked or crosslinked polymers, or mixtures of precursors thereof (such as monomers), especially synthetic materials such as described in items 1-29 of WO04106311 (see passage from bottom paragraph on page 48 until page 54, which is hereby incorporated by reference), where the term "materials comprising (especially consisting of) synthetic polymers or polymer precursors" especially relates to these materials as well as the further materials listed below and marked with an asterisk:

30.* Pre-polymeric monomers or oligomers of two or more of the aforementioned polymers or blends.

31.* Aqueous emulsions of natural and/or preferably *synthetic rubber, e.g. natural latex or preferably *latices of carboxylated styrene/butadiene copolymers.

32. Naturally occurring and synthetic* organic materials which are pure monomeric compounds or mixtures of such compounds, 33.* Sols, especially organosols, as stable liquid suspensions of colloidal nano-particles in a diluent, a reactive (e.g. crosslinking) diluent or in a polymerizable or crosslinking monomer, or in a mixture of all.

"Other monomeric compound" may, for example, refer to non-polymer materials, such as powders, dispersions or solutions of drugs (with or without carrier materials) or other smaller, non polymer chemical entities, e.g. with relative molecular weights up to 2000, preferably 1000 or lower.

The surface being coated (including laminated) and/or impregnated is the surface of any substrate (other word for material or product used herein) exposed to biofouling conditions. The substrate can be an inorganic or organic substrate, for example, based on a metal or metal alloy; a thermoplastic, elastomeric, inherently crosslinked or crosslinked polymer as described above; a natural polymer such as wood or rubber; a ceramic material; glass; a yarn; a non-woven material (e.g. for diapers or the like, such as PP non-wovens); paper; leather or other textile (e.g. for clothing, for technical purposes, for canvas or the like, e.g. from cotton, wool, latex and/or synthetic fibres.

The substrate may also be, for example, non-metal inorganic surfaces such as silica, silicon dioxide, titanium oxides, aluminum oxides, iron oxides, carbon, silicon, various silicates and sol-gels, masonry, and composite materials such as fiberglass and plastic lumber (a blend of polymers and wood shavings, wood flour or other wood particles).

The inorganic or organic substrate is, for example, a metal or metal alloy, a thermoplastic, elastomeric, inherently crosslinked or crosslinked polymer, a ceramic material or a glass.

The substrate may be a multi-layered article comprised of the same or different components in each layer. The surface coated, laminated and/or impregnated may be the exposed surface of an already applied coating or laminate.

The inorganic or organic substrate to be coated (this term including laminated) and/or impregnated can be in any solid form.

For example, polymer substrates may be plastics in the form of films, injection-molded articles, extruded workpieces, fibres, felts, non-woven or woven fabrics.

For example molded or extruded polymeric articles used in construction or the manufacture of durable goods such as siding, fascia and mailboxes can all benefit from the present method for stabilizer replenishment.

Plastics which would benefit from the uses or methods according to the invention include, but are not limited to, plastics used in construction or the manufacture of durable goods or machine parts, including outdoor furniture, boats, siding, roofing, glazing, protective films, decals, sealants, composites like plastic lumber and fiber reinforced composites, functional films including films used in displays as well as articles constructed from synthetic fibers such as awnings, fabrics such as used in canvas or sails and rubber articles such as outdoor matting and other uses cited in this disclosure. Exemplary of such plastics are polypropylene, polyethylene, PVC, POM, polysulfones, styrenics, polyamides, urethanes, polyesters, polycarbonate, acrylics, butadiene, thermoplastic polyolefins, ionomers, unsaturated polyesters and blends of polymer resins including ABS, SAN and PC/ABS.

The invention also provides a method of preventing biofouling of surfaces and/or materials, wherein a compound according to the invention is incorporated into a coating formulation or film which is then applied to the surface of an article.

Examples of applications of the antimicrobial compositions of the instant invention are surface coatings, protective paints, impregnation compositions, other coatings and laminates applied to vulnerable surfaces, for example, the hulls of ships, surfaces of docks or the inside of pipes in circulating or pass-through water systems, walls exposed to rain water, walls of showers, roofs, gutters, pool areas, saunas, floors and walls exposed to damp environs such as basements or garages, the housing of tools and outdoor furniture.

For example, the antimicrobial compositions of the instant invention are found, among other places, on the surfaces and/or in the materials of: boat hulls, docks, buoys, drilling platforms, ballast water tanks, machines, machine parts, recreational, air conditioning systems, ion exchangers, process water systems, other industrial water systems, solar-powered units, heat exchangers, sump pumps, drainage systems, roofing, basements, walls, facades, greenhouses, sheds, storage areas, awnings, garden fencing, wood protection, tent roof material, fabrics, outdoor furniture, door mats, public conveniences, bathrooms, showers, swimming pools, saunas, jointing, sealing compounds, public conveyances, locker rooms, and the like.

Process water includes any process water stream which is used for heating or cooling purposes in closed or open circulating systems.

In order to be active against microorganism and colonization by organisms, a compound or an antimicrobial composition according to the invention can, alternatively or in addition to being used for a coating and/or for impregnating, also be admixed to materials or intermediate products used to form products or articles, e.g. to oligomer- and or pre-polymer mixtures or melts (e.g. for extrusion or molding) or components used to form articles from natural or especially synthetic materials, or e.g. to glue or other binding materials used to bind wood or other chips in the production of pressboard or imitation pressboard, to adhesives, cements or other mortar or concrete components, to mortars, to resins, to solutions or the like.

The antimicrobial agents according to the present invention are also suitable as antimicrobials in cosmetic formulations, home care compositions or pharmaceutical compositions, collectively referred to as antimicrobial preparations hereinafter, especially to make use of their antimicrobial or preservative effect, further also for their anti-adhesion effects. For example, the antimicrobial agents cosmetic personal care applications such as deodorants, skin, hair and oral care products and rinse off products in home care applications for cleaning and disinfection of hard surfaces and fabric care applications such as liquid detergents and softeners, or in cosmetic formulations or pharmaceutical compositions. In each case, the amtimicrobial preparations may, in addition to the antimicrobial agent according to the present invention, comprise one or more than one further antimicrobial agent.

The antimicrobial preparations can be prepared by physically mixing the antimicrobial agent(s) with an adjuvant using customary methods, for example by simply stirring together the individual components, especially by making use of the dissolution properties of already known antimicrobial agents.

Further antimicrobials which can additionally be used in the present invention are known to those skilled in the art.

Combinations with chelating agents can also improve the antimicrobial activity of the antimicrobial agents of the present invention.

The antimicrobial preparations of the present invention can in addition comprise from about 0.05% to about 10% by weight of an anionic surfactant.

Non-limiting examples of anionic lathering surfactants useful in the compositions of the present invention are disclosed in McCutcheon's, Detergents and Emulsifiers, North American edition (1990), published by The Manufacturing Confectioner Publishing Co.; McCutcheon's, Functional Materials, North American Edition (1992); and U.S. Pat. No. 3,929,678, to Laughlin et al., issued Dec. 30, 1975, all of which are incorporated by reference.

The antimicrobial preparations of the present invention may further comprise a non-ionic surfactant. Typical non-ionic surfactants are condensated products of ethylene oxide with various reactive hydrogen-containing compounds reactive therewith having long hydrophobic chains.

The antimicrobial preparations of the present invention may also comprise a proton donating agent, most preferably from about 1% to about 5% by weight.

In order to achieve the mildness required of the antimicrobial preparation of the present invention, optional ingredients to enhance the mildness to the skin can be added. These ingredients include cationic and nonionic polymers, co-surfactants, moisturizers and mixtures thereof.

Another group of mildness enhancers are lipid skin moisturizing agents which provide a moisturizing benefit to the user when the lipophilic skin moisturizing agent is deposited to the user's skin. When in antimicrobial personal cleansing compositions herein lipophilic skin moisturizing agents are used, they are employed at a level of most preferably from about 0.5% to about 5% by weight of the composition.

A wide variety of lipid type materials and mixtures of materials are suitable for use in the antimicrobial preparations of the present invention. Preferably, the lipophilic skin conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. No. 3,600,186 to Mattson; Issued Aug. 17, 1971 and U.S. Pat. Nos. 4,005,195 and 4,005,196 to Jandacek et al; both issued Jan. 25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof. Fatty acids, fatty acid soaps and water soluble polyols are specifically excluded from our definition of a lipophilic skin moisturizing agent.

When a lipophilic skin moisturizing agent is employed as the mildness enhancer in the antimicrobial preparations herein, a stabilizer may also be included at a level preferably from about 0.1% to about 5% by weight of the antimicrobial preparation. The stabilizers used herein are not surfactants. The stabilizers provide improved shelf and stress stability.

The antimicrobial preparations of the present invention can comprise a wide range of optional ingredients. The CTFA International Cosmetic Ingredient Dictionary, Sixth Edition, 1995, which is incorporated by reference herein in its entirety, describes a wide variety of nonlimiting cosmetic and pharmaceutical ingredients commonly used in the skin care industry suitable for use in the antimicrobial preparations of the present invention. Nonlimiting examples of functional classes of ingredients are described at page 537 of this reference.

Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

The antimicrobial agents of the present invention can be used as ingredients in a wide variety of cosmetic preparations. There come into consideration, for example, especially one or more of the following preparations: skin-care preparations, bath preparations, cosmetic personal care preparations, foot-care preparations; light-protective preparations, skin-tanning preparations, depigmenting preparations, insect-repellents, deodorants, antiperspirants, preparations for cleansing and caring for blemished skin, hair-removal preparations in chemical form (depilation), shaving preparations, fragrance preparations or cosmetic hair-treatment preparations, or the like.

The final formulations may exist in a wide variety of presentation forms, for example in the form of liquid preparations as a W/O, O/W, O/W/O, W/O/W or PIT emulsion and all kinds of microemulsions, in the form of a gel, an oil, a cream, milk or lotion, a powder, a lacquer, a tablet or make-up, a stick, a spray or an aerosol, a foam, or a paste.

The antimicrobial agents of the present invention (especially those described as novel or regarding (methods of) their use with provisos as defined herein) can also be used against oral bacteria and to improve anti-plaque effectiveness, anti-gingivitis activities and to help to reduce paradontitis.

The activity can be improved by combinations with other antimicrobial actives or anti-plaque and anti-gingivitis actives such as for example chlorhexidine or phenolic substances such as 2,4,4'trichloro 2'-hydroxy diphenylether.

Typical oral preparations containing an antimicrobial agent of the present invention alone or in combinations with one or more of the above mentioned antimicrobials and anti-plaque agents are e.g. mouthrinses, semi-solids such as toothpastes or gel dentifrices, chewing gums or solid lozenge or the like.

Furthermore, an oral composition may comprise:

polishing agents, humectants, water, natural or synthetic thickener or gelling agent, alcohol such as ethanol or isopropanol, organic surface-active agents which can be cationic, anionic or non-ionic, flavoring agents, sweetening agents, agents used to diminish teeth sensitivity, whitening agents such as urea peroxide and hydrogene peroxide, preservatives such as sodium benzoate, substances which release fluoride ions to protect against caries, and/or other agents such as chlorophyll compounds and/or ammoniated materials such as urea, diammonium phosphate and mixtures thereof.

Antibacterial enhancing agents may be included in the oral composition.

Preferably, the antibacterial enhancing agent is an anionic polymer comprising a chain or backbone containing repeating units each preferably containing at least one carbon atom and preferably at least one directly or indirectly pendent, monovalent delivery-enhancing group and at least one directly or indirectly pendent monovalent retention-enhancing group geminally, vicinally or less preferable otherwise bonded to atoms, preferably carbon, in the chain.

The antimicrobial agents of the present invention can also be used as additives in laundry detergent and/or fabric care compositions, especially under consideration of the provisos regarding their use. The laundry detergent and/or fabric care compositions of the present invention preferably further comprise a detergent ingredient selected from cationic, anionic and/or nonionic surfactants and/or bleaching agent.

The antimicrobial laundry detergent and/or fabric care compositions according to the invention can be liquid, paste, gels, bars, tablets, spray, foam, powder or granular forms. Granular compositions can also be in "compact" form, the liquid compositions can also be in a "concentrated" form.

The compositions of the invention may, for example, be formulated as hand and machine laundry detergent compositions.

When formulated as compositions suitable for use in a laundry machine washing method, the laundry detergent and/or fabric care compositions of the invention preferably comprise both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components.

The laundry detergent and/or fabric care compositions of the present invention may also contain cationic fabric softening components which include the water-insoluble quaternary-ammonium fabric softening actives or the corresponding amine precursor, the most commonly used having been di-long alkyl chain ammonium chloride or methyl sulfate.

The laundry detergent and/or fabric care compositions of the present invention may also contain ampholytic, zwitterionic, and semi-polar surfactants.

The laundry detergent and/or fabric care compositions may further comprise one or more enzymes which provide cleaning performance, fabric care and/or sanitisation benefits. The antimicrobial laundry detergent compositions according to the present invention may further comprise a builder system. Any conventional builder system is suitable for use herein. The antimicrobial laundry detergent and/or fabric care compositions herein may also optionally contain one or more iron and/or manganese chelating agents.

The antimicrobial laundry detergent compositions herein may also contain water-soluble methyl glycine diacetic acid (MGDA) salts (or acid form) as a chelant or co-builder useful with, for example, insoluble builders such as zeolites, layered silicates and the like.

Another optional ingredient is a suds suppressor, exemplified by silicones, and silica-silicone mixtures.

Other components such as soil-suspending agents, soil-release agents, optical brighteners, abrasives, bactericides, tarnish inhibitors, colouring agents, and/or encapsulated or non-encapsulated perfumes may be employed.

The laundry detergent and/or fabric care composition of the present invention can also contain dispersants: Suitable water-soluble organic salts are the homo- or co-polymeric acids or their salts, in which the polycarboxylic acid comprises at least two carboxyl radicals separated from each other by not more than two carbon atoms.

The laundry detergent and/or fabric care compositions of the present invention can also include compounds for inhibiting dye transfer from one fabric to another of solubilized and suspended dyes encountered during fabric laundering operations involving coloured fabrics.

The antimicrobial agents according to the present invention can also be applied to textiles, which treatment can be carried out before dyeing of the textiles, during dyeing or after dyeing (as an after-treatment). The application of the antimicrobials can, for example, be carried out by an exhaustion process, padding, spraying or by foam application.

The antimicrobial agents according to the present invention may be applied as aqueous formulation in diluted, solubilized, emulsified or dispersed form.

Such aqueous formulations can additionally comprise a small amount of an organic solvent, a surfactant, a dispersant, and/or an emulsifier.

Padding can be carried out according to conventional padding processes. For example, the textile material is passed through an aqueous liquor comprising the antimicrobial agent, the textile material is squeezed to a defined liquor pick-up rate and then a fixation step is carried out, preferably a heat treatment.

The amount of the antimicrobial agent according to the present invention in the aqueous liquor (padding liquor) is usually 0.001% to 10% by weight, an amount of the antimicrobial agent of 0.01% to 5% by weight is preferred.

The fixation step is usually carried out by a heat treatment, for example at a temperature of 60 to 150° C., especially 90 to 150° C.

The padding process is usually carried out as a continuous process wherein the textile material is continuously passed through the aqueous liquor containing the antimicrobial agent.

The application of the antimicrobial agent according to the exhaustion process is usually carried out from an aqueous liquor, at a pH value of from 2 to 9, from 4 to 7, and a temperature from 50 to 100° C. and especially from 80 to 100° C. The liquor ratio selected can vary within a wide range, for example from 1:5 to 1:50, preferably from 1:5 to 1:30.

The amounts in which the antimicrobial agents are used in the dye baths may vary within wide limits; amounts of from 0.01 to 10% by weight, especially from 0.01 to 5% by weight, based on the goods to be treated, have generally proved advantageous.

Spraying can be carried out according to conventional spraying processes. According to these processes aqueous liquids comprising the antimicrobial agent according to the present invention are sprayed onto the textile material. The amount of the antimicrobial agent in the aqueous liquor is usually 0.001% to 10% by weight, especially 0.01% to 10% by weight, based on the weight of the aqueous liquor. An amount of the antimicrobial agent of 0.1% to 10% by weight is preferred. Such spraying processes are especially suitable for applying the antimicrobial agent to textile materials like carpets. According to such preferred processes a plurality of spray nozzles are disposed in a spray line transverse to the direction of movement of, for instance, the carpet. The antimicrobial agent is applied as an aqueous liquor by the spray nozzles, for example by virtue of pressure.

After spraying, usually a fixation step is carried out, which can be performed by a heat treatment as given above for the padding process.

Spraying can also be used to apply the antimicrobial agent in form of an aqueous liquor to surfaces of textile materials including leather, like sofas or shoes.

The antimicrobial agent according to the present invention can also be applied to the textile material by foam application. As to this application all of the above conditions and preferences given above for the spraying process apply. However, the antimicrobial agent according to the present invention is applied in form of an aqueous foam which usually in addition contains a foam stabiliser and may comprise other customary additives. Such a process is also especially suitable for treating carpets.

Exhaustion, padding, spraying or foam applications can be carried out by applying the antimicrobial agent to the textile material together with dyestuffs (for example in a dyeing process) or in other textile related processes, like finishing processes. It is preferred to carry out the treatment with the antimicrobial agents in the presence of dyestuffs.

If these processes are carried out without the presence of dyestuffs it is preferred to apply the antimicrobial agent in a finishing process.

The use of some polymeric as well as oligomeric substances that are commonly used in the textile industries, can help to further improve the durability of the desirable antimicrobial efficacy. Such substances include, but are not limited to, resin finishings that provide easy care and/or other properties to various textile materials, softeners, coating materials, fixation agents and/or other finishing agents such as hydrophilic and hydrophobic agents, flame retardant etc. It is obvious, from economic as well as process convenience perspective that the antimicrobial treatment could be carried out together with many other different types of treatments that are found in the textile industries.

The application of the antimicrobial agent according to the present invention can also be carried out in a dyeing process. For such processes the above conditions and preferences apply. Suitable dyes are disperse dyes, basic dyes, acid dyes, direct dyes or reactive dyes. Reactive dyes are especially suitable for natural polyamide- or cellulose-containing textile materials. Direct dyes are especially suitable for cellulose-containing textile materials. The dyes may belong to different dye classes, including acridone, azo, anthraquinone, coumarin, formazane, methine, perinone, naphthoquinone-imine, quinophthalone, styryl or nitro dyes. Mixtures of dyes may also be used.

When using the antimicrobial agent in a dyeing process, the procedure can be such that the textile material is first treated with these compounds and then dyeing is carried out or, preferably, the textile material is treated simultaneously with the antimicrobial agent and the dye. The application of the antimicrobial agent can, however, also be effected subsequently to the previously prepared dyeing.

After the dyeing process including the application of the antimicrobial agent according to the present invention the textile material can be subjected to a fixation step, like a heat treatment as given above.

Textile materials which can be treated with the antimicrobial agents are materials comprising, for example, natural or synthetic polyamide (like wool, silk, nylon), polyurethane, polyester, polypropylene, polyethylene, polyacrylonitrile and cellulose-containing textile materials of all kinds, for example natural cellulose fibres, such as cotton, linen, jute and hemp, and also viscose staple fibre and regenerated cellulose; or blends of the above fibre materials, like polyacrylonitrile/polyester, polyamide/polyester, polyester/cotton, polyester/viscose and polyester/wool.

Preferred textile materials are those comprising wool, synthetic polyamide, polyester, polypropylene, polyethylene, and cellulose-containing textile materials, preferably cotton or wool and especially cotton.

The textile material can be in different forms of presentation, as woven or knitted fabrics or as piece goods such as knitgoods, nonwoven textiles, carpets, yarn or staple fibres. Preferred are nonwoven textile materials and especially carpets.

Numerous end use articles can be named for the treated fabrics or products made from the materials containing a compound of the invention. Examples include but are not limited to carpets and rags, pillow cases, bed linings, bed sheets, matrices and matrices ticking, curtains, duvet and duvet cases, upholsteries, socks, shoes, shoe inlays, garments.

The antimicrobial and (especially with regard to colonization by organisms, especially microorganisms) anti-adhesive properties of the compounds of the present invention can be determined according to standard procedures, e.g. by the methods mentioned in the Examples. Such assays show a good to very good antimicrobial activity of the compounds according to the invention.

The following examples are for illustrative purposes only and are not to be construed to limit the instant invention in any manner whatsoever. Room temperature (r.t.) depicts a temperature in the range 20-25° C.; over night denotes a time period in the range 12-16 hours. Percentages are by weight unless otherwise indicated.

Abbreviations used in the examples or elsewhere:
M concentration in moles per liter
DMF dimethylformamide
MS mass spectrometry
GC gas chromatography
PMMA poly methylmethacrylate

PREPARATION EXAMPLES

Educts

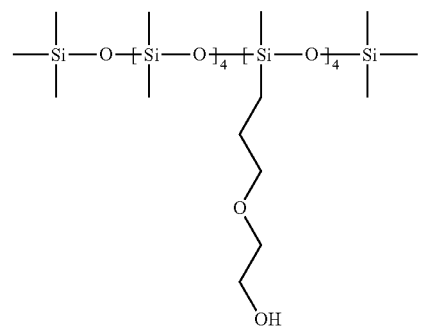

Educt A

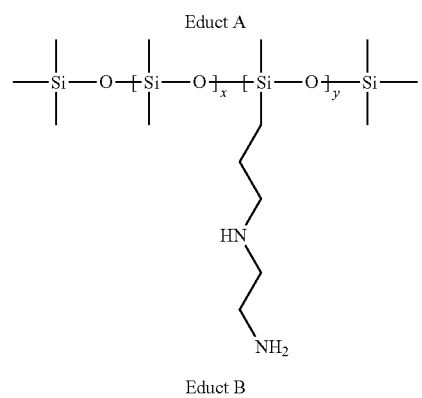

Educt B

Educts A and B contain the repeating units in statistical order. Educt B contains an average number of 250 Si atoms in the chain, with x:y standing in a ratio of approximately 10:1. Both educts are available from Wacker, Germany.

Synthesis of 11-bromoundecanoyl chloride 20.0 g of 11-bromoundecanoic acid (0.0754 mol) are placed in 20 ml dichloromethane in the presence of 0.28 g DMF (0.05 eq). The reaction mixture is heated to reflux and 10.68 g of thionyl chloride (0.0905 mol) are added drop wise over a period of 1 h 40 min at 39° C. After 3 h at 39° C. the reaction mixture is cooled down to r.t. and evaporated to dryness, yielding to 7.9 g of the expected compound.

Examples 1-3

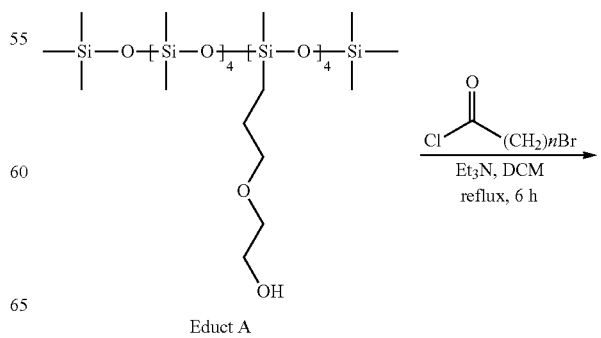

Educt A ppm, 16H; m, 2.2 ppm, 8H; s, 3 ppm, 24H; m, 3.15 ppm, 16H; t, 3.3 ppm, 8H; t, 3.5 ppm, 8H; t, 4.05 ppm, 8H.

3. Quaternisation of Polymer A1 with Pyridine Yielding Polymer A3

The procedure of example 2 is repeated except that N,N-dimethyldecylamine is replaced by the equivalent amount of pyridine. Polymer A3 is obtained as a dark yellow oil.

NMR in CD2Cl2:

S, 0 ppm, 54H; m, 0.45 ppm, 8H; m, 1.2 ppm, 40H; m, 1.5 ppm, 16H; m, 1.9 ppm, 8H; t, 2.2 ppm, 8H; s, 3.2 ppm, 8H; m, 3.3 ppm, 8H; m, 3.5 ppm, 8H; m, 4.05, 8H; m, 4.5 8H; m, 8, 8H); f, 8.5, 4H; s, 8.9 ppm, 8H.

Examples 4-5 (n=10)

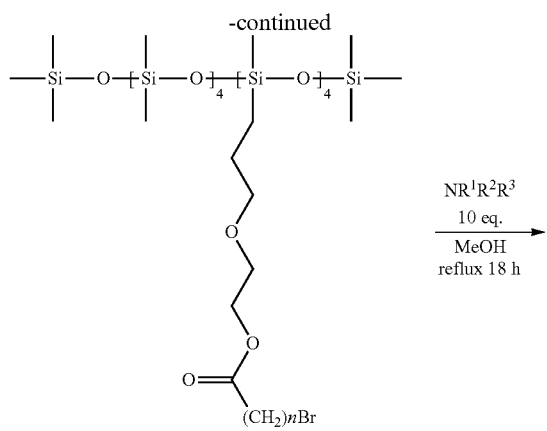

Example 1
(n = 10)

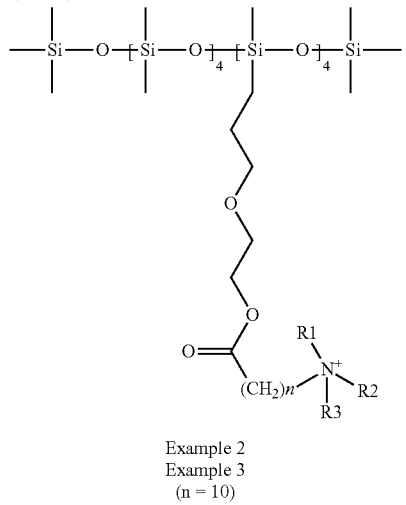

Example 2
Example 3
(n = 10)

1. Functionalisation of the siloxane carbinol (A) with 11-bromoundecanoyl chloride (Polymer A1, $R_5$=bromodecyl)

15.21 g of Educt A (0.01375 mol alcohol functionality) is diluted in 60 ml dichloromethane with 5.56 g of triethylamine (0.055 mol). The mixture is heated to 40° C. and 15.59 g of 11-bromoundecanoyl chloride (0.055 mol) are added dropwise over 40 min. (exotherm). After 7 h at 40° C. the mixture is cooled down to r.t. and washed with 3 times water/acetic acid (pH 2). The organic layer is evaporated to dryness, yielding 27.5 g of polymer A1 as a yellow oil.

NMR in CD2Cl2:

S, 0 ppm, 54H; m, 0.4 ppm, 8H; m, 1.2 ppm, 40H; m, 1.3 ppm, 8H; m, 1.5 ppm, 16H; m, 1.75 ppm, 8H; t, 2.2 ppm, 8H; m, 3.3 ppm, 16H; t, 3.5 ppm, 8H; t, 4.05 ppm, 8H

2. Quaternisation of the Polymer A1 with N,N-dimethyldecylamine Yielding Polymer A2

9 g of the product of example 1 (0.0043 mol) and 31.88 g of N,N-dimethyldecylamine (0.1720 mol) are placed together and heated at 66° C. for 72 h. After cooling, the oily product is washed 4 times with hexane. The product is evaporated to dryness, yielding 10.95 g of Polymer A2 a dark yellow oil.

GC control shows 4-5% remaining free amine.

NMR in CD2Cl2: s, 0 ppm, 54H; m, 0.4 ppm, 8H; t, 0.8 ppm, 12H; m, 1.25 ppm, 104H; m, 1.5 ppm, 16H; m, 1.65

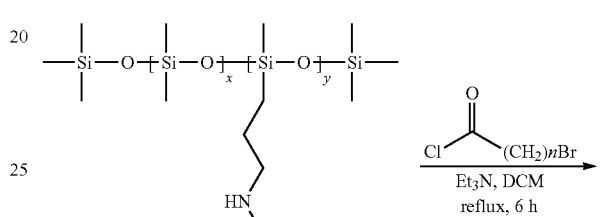

Educt B

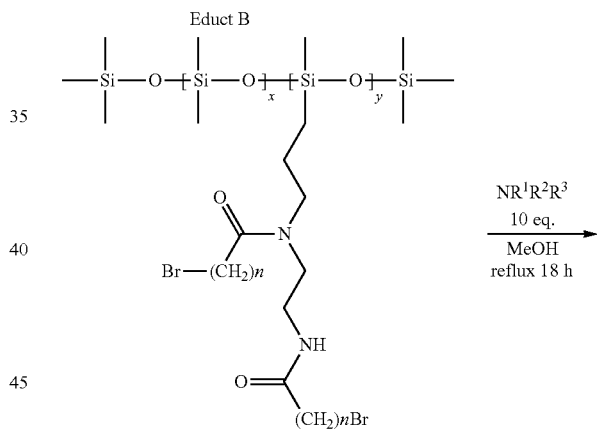

Example 4

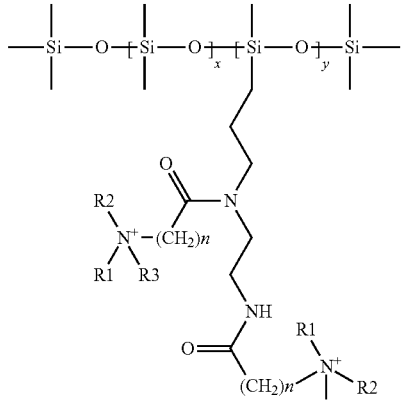

Example 5

4. Functionalisation of the Educt B with 11-bromoundecanoyl chloride (Polymer B1, $R_5$=bromodecyl)

The procedure of example 1 is repeated except that 0.01375 mol alcohol functionality of Educt A is replaced by Educt B in an amount corresponding to 0.01375 mol of total nitrogen functionality, and the equivalent amount of 11-bromoundecanoyl chloride is used. Polymer B1 is obtained as a yellow oil.

5. Quaternisation of Polymer B1 with Pyridine Yielding Polymer B2

The procedure of example 2 is repeated except that educt Polymer A1 is replaced by the equivalent amount of Polymer B1 as the educt, and N,N-dimethyldecylamine is replaced by twice the equivalent amount of pyridine. Polymer B2 is obtained as a dark yellow oil. NMR in CD2Cl2 confirms the expected structure.

Example 6

Functionalisation of Educt B with 4-chloro-6-methyl-2-phenylpyrimidine

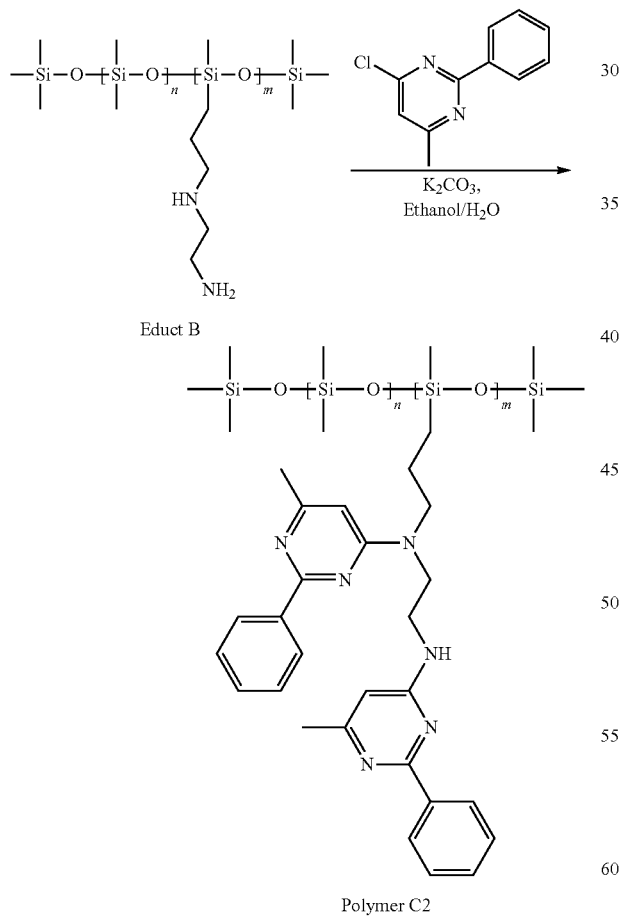

Polymer C2

4-chloro-6-methyl-2-phenylpyrimidine is prepared according to the method described in WO2003077656.

4.17 g of Educt B are reacted with 1.88 g of 4-chloro-6-methyl-2-phenylpyrimidine (0.0092 mol) in ethanol/water (8/12 ml) in the presence of potassium carbonate (1.27 g, 0.0092 mol) at 76° C. for 50 h. After 24 hours, 5 ml of dioxane are added to improve the solubility of the system. After cooling the reaction mixture is diluted with 50 ml dichloromethane and washed 3 times with water and sodium hydroxide at pH 12 and 7. The organic phase is evaporated to dryness to give 3.9 g of functionalised polysiloxane (Polymer C2).

Example 7

Functionalisation of Educt B with Benzyl Bromide

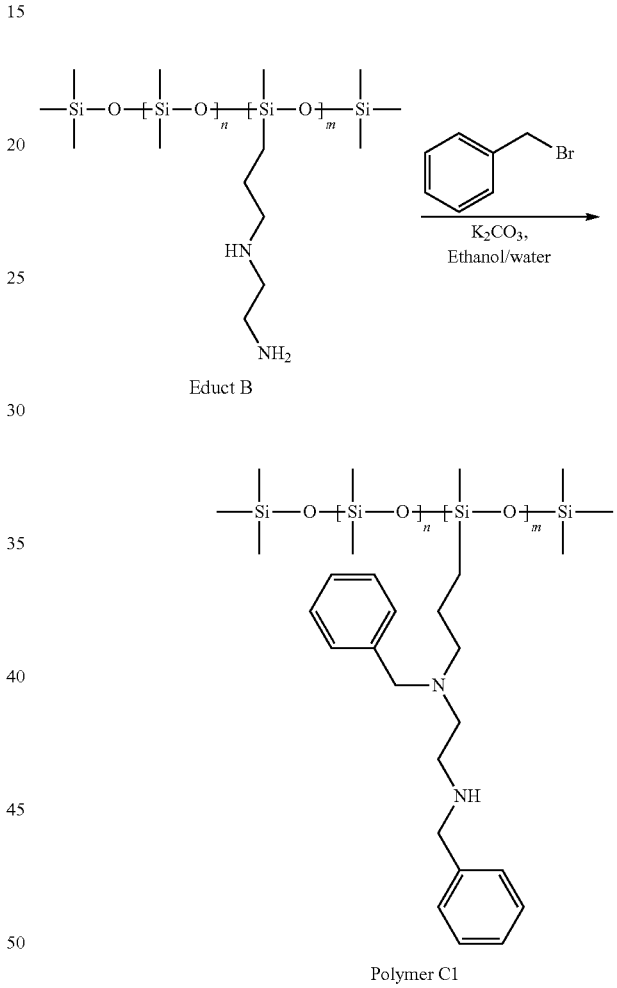

Polymer C1

The procedure of example 6 is repeated except that 4-chloro-6-methyl-2-phenylpyrimidine is replaced by the equivalent amount of benzyl bromide. Polymer C1 is obtained as a dark yellow oil. NMR in CD2Cl2 confirms the expected structure.

The polymers of examples 8-24 (see table below) are prepared in analogy to the above examples using the appropriate educts and reagents (i.e. Educt A for all polymers of type A, Educt B for all polymers of types B and C; analogous reagents suitable to introduce residues CORX or X). Assay numbers refer to the application examples further below.

TABLE 1

Compilation of preparation examples

Polymer Type A

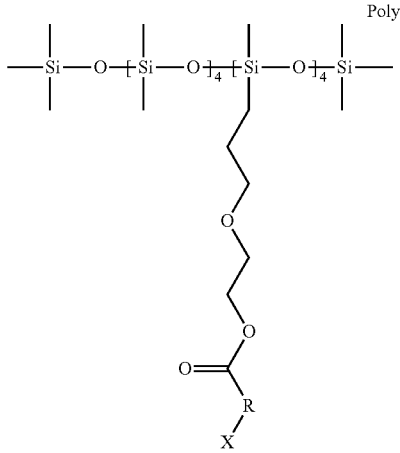

Polymer Type B

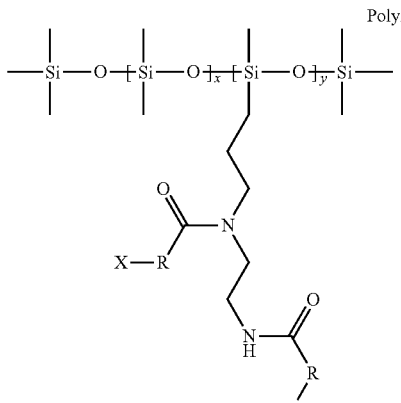

Polymer Type C

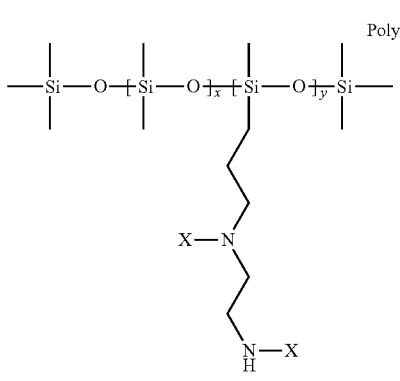

TABLE 1-continued

| Example | Assay | Polymer Type | R | X |
|---|---|---|---|---|
| 3 | 1 | A | decyl | pyridyl* |
| 5 | 2 | B | decyl | pyridyl* |
| 8 | 3 | A | heptyl | pyridyl* |
| 9 | 4 | B | heptyl | pyridyl* |
| 10 | 5 | A | benzyl | pyridyl* |
| 11 | 6 | A | decyl | triethylammonium |
| 12 | 7 | B | decyl | triethylammonium |
| 13 | 8 | A | decyl | cyclohexyldimethylammonium |
| 14 | 9 | B | decyl | cyclohexyldimethylammonium |
| 15 | 10 | A | heptyl | cyclohexyldimethylammonium |
| 16 | 11 | B | heptyl | cyclohexyldimethylammonium |
| 2 | 12 | A | decyl | decyldimethylammonium |
| 17 | 13 | B | decyl | decyldimethylammonium |
| 18 | 14 | A | heptyl | decyldimethylammonium |
| 19 | 15 | B | heptyl | decyldimethylammonium |
| 20 | 16 | B | decyl | benzyldimethylammonium |
| 21 | 17 | A | heptyl | benzyldimethylammonium |
| 22 | 18 | B | heptyl | benzyldimethylammonium |
| 1 | 19 | A | decyl | Br |
| 4 | 20 | B | decyl | Br |
| 23 | 21 | A | heptyl | Br |
| 24 | 22 | A | benzyl | Br (bonding on aliphatic C) |
| 7 | 23 | C | — | benzyl |
| 6 | 24 | C | — | 2-phenyl-4-methylpyrimid-6-yl |

*N-bonded (quaternized)

APPLICATION EXAMPLES

A) Microbicidal Activity

1. Microbicidal Activity According to EN1040

A bacterial suspension with a cell count of about $10^7$ cfu/ml is contacted with appropriate concentrations of the specific substances and the residual cell count is determined after incubation times of 5 and 30 min. at room temperature under continuous stirring. *Staphylococcus aureus* is tested as gram+ and *Escherichia coli* as gram– organism. The results in Tab. 2 are given as a log reduction in comparison to a growth control in water. Higher numbers denote better microbiocidal activity.

TABLE 2

Microbicidal activity against gram positive and gram negative bacteriae

| | S. aureus | | | | E. coli | | | |
|---|---|---|---|---|---|---|---|---|
| Assay | Log red 100 ppm 5 min | Log red. 100 ppm 30 min | Log red 1000 ppm 5 min | Log red. 1000 ppm 30 min | Log red. 100 ppm 5 min | Log red. 100 ppm 30 min | Log red. 1000 ppm 5 min | Log red. 1000 ppm 30 min |
| 1 | 2.8 | >5 | 4.7 | >5 | >5 | >5 | >5 | >5 |
| 2 | 1.4 | 4.3 | 3.3 | >5 | >5 | >5 | >5 | >5 |
| 3 | | | 4.8 | >5 | | | >5 | >5 |
| 4 | | | 3.7 | >5 | | | >5 | >5 |
| 5 | | | 4.2 | >5 | | | >5 | >5 |

TABLE 2-continued

Microbicidal activity against gram positive and gram negative bacteriae

| | S. aureus | | | | E. coli | | | |
|---|---|---|---|---|---|---|---|---|
| Assay | Log red. 100 ppm 5 min | Log red. 100 ppm 30 min | Log red. 1000 ppm 5 min | Log red. 1000 ppm 30 min | Log red. 100 ppm 5 min | Log red. 100 ppm 30 min | Log red. 1000 ppm 5 min | Log red. 1000 ppm 30 min |
| 6 | <1 | <1 | <1 | 1.9 | >5 | >5 | >5 | >5 |
| 7 | <1 | <1 | 2.3 | >5 | >5 | >5 | >5 | >5 |
| 8 | 1.1 | 4 | 5 | >5 | >5 | >5 | >5 | >5 |
| 9 | 1.4 | 4.4 | 3.6 | >5 | >5 | >5 | >5 | >5 |
| 10 | | | <1 | <1 | | | >5 | >5 |
| 11 | | | 1.4 | 2.4 | | | >5 | >5 |
| 12 | <1 | >5 | >5 | >5 | >5 | >5 | >5 | >5 |
| 13 | <1 | 2.4 | >5 | >5 | >5 | >5 | >5 | >5 |
| 14 | | | >5 | >5 | | | >5 | >5 |
| 15 | | | >5 | >5 | | | >5 | >5 |
| 16 | 1.4 | >5 | >5 | >5 | >5 | >5 | >5 | >5 |
| 17 | | | 3.8 | >5 | | | >5 | >5 |
| 18 | | | 1.8 | 2.3 | | | >5 | >5 |
| 19 | | | <1 | 1.1 | | | <1 | <1 |
| 20 | | | <1 | 1.8 | | | <1 | <1 |
| 21 | | | <1 | 1.1 | | | <1 | <1 |
| 22 | | | <1 | 2.8 | | | >5 | >5 |
| 23 | | | 4.8 | 4.9 | | | >5 | >5 |
| 24 | | | 2.8 | >5 | | | >5 | >5 |

2. Microbicidal Activity Under Conditions of a Preservative Challenge Test

*P. aeruginosa* and *E. Coli* represents Gram− bacteria, *S. aureus* the Gram+ bacteria, *C. albican* the yeast and *A. niger* the fungi. Test procedure is as described above, with an inoculum concentration of $10^5$ cfu/ml and incubation times of 48 and 72 h. Figures in the below table are given as log reduction.

TABLE 3

| Assay | Conc. [%] | PEG40 Castor Oil | Ps. aeruginosa ATCC 15442 48 h | 72 h | E. coli ATCC 10536 48 h | 72 h | S. aureus ATCC 6538 48 h | 72 h | C. albicans ATCC 10231 48 h | 72 h | A. niger ATCC 16404 48 h | 72 h |
|---|---|---|---|---|---|---|---|---|---|---|---|---|
| 12 | 0.1 | | >3 | >3 | >3 | >3 | >3 | >3 | >3 | >3 | 1.7 | 1.8 |
| 1 | 0.1 | | >3 | >3 | >3 | >3 | >3 | >3 | >3 | >3 | <1 | <1 |
| 2 | 0.1 | | >3 | >3 | >3 | >3 | >3 | >3 | >3 | >3 | <1 | <1 |
| 12 | 0.5 | | >3 | >3 | >3 | >3 | >3 | >3 | >3 | >3 | >3 | >3 |
| 12 | 0.5 | 1% | >3 | >3 | >3 | >3 | >3 | >3 | >3 | >3 | 2.4 | 2.9 |
| 1 | 0.5 | | >3 | >3 | >3 | >3 | >3 | >3 | >3 | >3 | <1 | <1 |
| 1 | 0.5 | 1% | >3 | >3 | >3 | >3 | >3 | >3 | <1 | >3 | <1 | <1 |
| 2 | 0.5 | | >3 | >3 | >3 | >3 | >3 | >3 | 2.0 | 2.9 | <1 | <1 |
| 2 | 0.5 | 1% | >3 | >3 | >3 | >3 | >3 | >3 | 1.7 | 2.5 | <1 | <1 |

B) Antifungal Activity

Fungicidal activity is tested according to EN12175. A fungal spore suspension with a spore cell count of about $10^6$ cfu/ml is contacted with appropriate concentrations of the specific substances and the residual spore cell count is determined after incubation times of 30 and 60 min. at room temperature under continuous stirring. *Penicillium funiculosum*, *Aspergillus niger* and *Aureobasidium pullulans* are tested as important mold strains.

The results in Tab. 4 are given as log reduction at each incubation time in comparison to a water control (higher numbers denote better microbiocidal activity).

TABLE 4

| Assay | | P. funiculosum | | A. niger | | A. pullulans | |
|---|---|---|---|---|---|---|---|
| | | 30 min | 1 h | 30 min | 1 h | 30 min | 1 h |
| 23 2500 ppm | 30' 1 h | 1.2 | 2.1 | 3.9 | >4 | >4 | >4 |

TABLE 4-continued

| Assay | | P. funiculosum | | A. niger | | A. pullulans | |
|---|---|---|---|---|---|---|---|
| | | 30 min | 1 h | 30 min | 1 h | 30 min | 1 h |
| 14 5000 ppm | 30' 1 h | 1.0 | 2.1 | 1.7 | 3.0 | >4 | >4 |

C) Antiadhesion

The antiadhesive efficacy is tested after temporary attaching various compounds to a PMMA test specimen by incubation of the test specimen in a 0.5% solution of the polymer to be tested. The test is carried out in analogy to the method described by Bechert et al., Nature Med. 6 (No. 8, September 2000), p. 1053. Then, the coated specimen is dried and incubated in a suspension of Staphylococcus aureus cells for 1 hour at 30° C. under shaking. After washing, the attached cells are detected via binding of a primary antibody and—after incubation of night and further washing steps—binding of a secondary antibody with alkaline phosphatase attached. The adhesion is then determined in a colorimetric assay in comparison to an untreated PMMA test specimen, which is calculated as showing 100% adhesion. Results compiled in the following Tab. 5 are given as residual adhesion on the pre-coated surface.

TABLE 5

| Assay | Test conc. [%] | Residual adhesion [%] |
|---|---|---|
| 19 | 0.5 | 110 |
| 20 | 0.5 | 84 |
| 9 | 0.5 | 52 |
| 13 | 0.5 | 78 |
| 16 | 0.5 | 59 |
| 1 | 0.5 | 46 |
| 2 | 0.5 | 54 |
| 22 | 0.5 | 76 |
| 21 | 0.5 | 100 |

D) Biofilm Inhibition

The ability of inhibiting the initial stages of biofilm formation is tested in a microplate based screening assay. Standard test specimen made of polycarbonate are contacted with a solution of the polymer to be tested in water or ethanol at a concentration of 0.5% for ½ hour, in order to allow the compounds to form a film on the pin surface. The pins are then dried at room temperature under laminar flow. The coated pins are contacted with a bacterial inoculum of Staphylococcus aureus at a cell count of $10^4$-$10^5$ cfu/ml in a microplate and a biofilm is allowed to form on the plastic surface over 24 hours. Loosely attached cells are then rinsed off in a couple of rinsing steps, then the biofilm on the surface is removed by ultrasonic treatment. The eluted cell count is either determined via conventional cell count technique (dilution series and surface plate count; see Table 6).

TABLE 6

| | log reduction per cm² of precoated standard surface | |
|---|---|---|
| Assay | pID | log reduction as compared to growth control |
| 19 | 189 | 0.0 |
| 20 | 190 | 0.0 |
| 9 | 203 | >5 |
| 13 | 204 | 0.4 |
| 16 | 205 | 1.0 |
| 1 | 206 | >5 |
| 2 | 207 | >5 |
| 22 | 208 | 1.0 |
| 21 | 209 | 0.1 |

The invention claimed is:

1. An antimicrobial composition comprising (A) an organic or inorganic carrier and
    (B) an oligo- or polysiloxane compound, or salt thereof, wherein said compound comprises at least 3, Si atoms in the main chain, and wherein at least one thereof is contained in a moiety of formula I

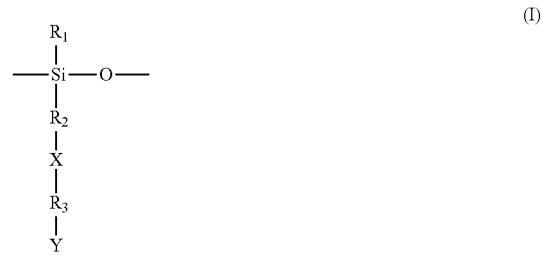

wherein said formula (I) comprises an open bond of the O atom is linked to another Si atom of the oligo- or polysiloxane main chain, and said open bond of the Si atom is linked either to another O atom of the oligo- or polysiloxane main chain or to $R'_1$, where
$R_1$ and $R'_1$ independently are $C_1$-$C_{10}$alkyl,
$R_2$ and $R_3$ independently are $C_1$-$C_{18}$alkylene,
X is a divalent spacer group selected from the group consisting of O, $NR_4$, $N(COR'_5)$, $CONR'_4$, and $OCONR'_4$;
Y is selected from the group consisting of $OCOR_5$, $NHCOR_5$, $NHR_4$, $COOR_5$, $CONHR_4$, and $NR'_4R_4$;
$R_4$ is selected from a $C_6$-$C_{18}$ organic residue containing at least one aryl moiety, pyridyl, pyrimidyl, pyridylium, pyrimidylium and triazinyl;
$R'_4$ is as defined for $R_4$; or is selected from the group consisting of H, $C_1$-$C_{20}$alkyl, $C_7$-$C_{20}$-phenylalkyl, and $C_4$-$C_{12}$cycloalkyl;
$R_5$ is $R_7$—Z;
$R'_5$ is as defined for $R_5$; or is selected from the group consisting of H, $C_1$-$C_{20}$alkyl, $C_7$-$C_{20}$-phenylalkyl, and $C_4$-$C_{12}$cycloalkyl;
$R_7$ is $C_6$-$C_{18}$alkylene, which may be interrupted by phenylene, $C_4$-$C_{12}$cycloalkylene, O, or $NR'_4$; or is unsubstituted or substituted phenylene or $C_4$-$C_{12}$cycloalkylene;
Z is halogen or $N^+R_8R_9R_{10}$;
$R_8$, $R_9$ and $R_{10}$ independently are selected from the group consisting of $C_1$-$C_{20}$alkyl, $C_7$-$C_{20}$-phenylalkyl, $C_4$-$C_{12}$cycloalkyl, and unsubstituted or substituted aryl; or 2 of $R_8$, $R_9$ and $R_{10}$ are linked together to form a quaternized aliphatic, substituted or unsubstituted N-heterocyclic ring of 4-6 carbon atoms; or all of $R_8$, $R_9$ and $R_{10}$ are linked together to form, together with the nitrogen atom they are bonding to, a substituted or unsubstituted N-heterocyclic ring system of 4-7 carbon atoms.

2. The composition according to claim 1, wherein the compound containing the moiety of the formula I is of formula II

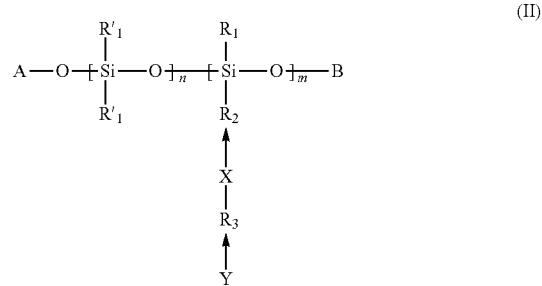

wherein m is selected from the range 1-1000, and n is selected from the range 0-1000; $R_1$, $R'_1$, $R_2$, $R_3$, X and Y are as defined in claim 1, and A and B independently are groups of the formula —Si($R_{11}R_{12}R_{13}$), wherein each of $R_{11}$, $R_{12}$, $R_{13}$ independently is as defined for $R_1$, or A and B together may form a direct bond.

3. The composition according to claim 1, where
$R_1$ and $R'_1$ independently are $C_1$-$C_4$alkyl,
$R_2$ and $R_3$ independently are $C_2$-$C_{12}$alkylene,
X is a divalent spacer group selected from the group consisting of O, $NR_4$, and $N(COR_5)$;
Y is selected from the group consisting of $OCOR_5$, $NHCOR_5$, $COOR_5$, $CONHR_4$, and $NR'_4R_4$;
$R_4$ is $C_4$-$C_{10}$aryl moiety or $C_1$-$C_{12}$alkyl moiety substituted by $C_4$-$C_{10}$aryl or $C_2$-$C_{12}$ alkyl interrupted by $C_4$-$C_{10}$arylene, wherein each aryl or arylene may be unsubstituted or substituted;
$R'_4$ is as defined for $R_4$; or is selected from the group consisting of H, $C_1$-$C_{20}$alkyl, and $C_4$-$C_{12}$cycloalkyl;
$R_5$ is $R_7$—Z;
$R_7$ is $C_6$-$C_{18}$alkylene; $C_1$-$C_{20}$alkylene interrupted by phenyl, $C_4$-$C_{12}$cycloalkylene, O, or $NR'_4$; or is unsubstituted or substituted phenylene or $C_4$-$C_{12}$cycloalkylene;
Z is halogen or $N^+R_8R_9R_{10}$;
$R_8$, $R_9$ and $R_{10}$ independently are selected from the group consisting of $C_1$-$C_{20}$alkyl, $C_7$-$C_{20}$-phenylalkyl, $C_4$-$C_{12}$cycloalkyl, and unsubstituted or substituted aryl; or 2 of $R_8$, $R_9$ and $R_{10}$ are linked together to form a quaternized aliphatic, substituted or unsubstituted N-heterocyclic ring of 4-6 carbon atoms; or all of $R_8$, $R_9$ and $R_{10}$ are linked together to form, together with the nitrogen atom they are bonding to, a substituted or unsubstituted N-heterocyclic ring system of 4-7 carbon atoms.

4. The composition according to claim 1, where
$R_1$ and $R'_1$ independently are $C_1$-$C_4$alkyl,
$R_2$ and $R_3$ independently are $C_2$-$C_{12}$alkylene,
X is a divalent spacer group selected from the group consisting of O, $NR_4$, and $N(COR_5)$;
Y is selected from the group consisting of $OCOR_5$, $NHCOR_5$, $COOR_5$, $CONHR_4$, and $NR'_4R_4$;
$R_5$ is $R_7$—Z;
$R_4$ is phenyl, naphthyl, pyridyl, pyrimidyl, pyridylium, pyrimidylium, triazinyl; or $C_1$-$C_8$alkyl substituted by phenyl, naphthyl, pyridyl, pyrimidyl, pyridylium, pyrimidylium, triazinyl; or phenyl, naphthyl, pyridyl, pyrimidyl, pyridylium, pyrimidylium, triazinyl, each of which is substituted by $C_1$-$C_8$alkyl, halogen, amino, phenyl, $C_1$-$C_4$alkylphenyl, benzyl; or $C_1$-$C_8$alkyl, which is substituted by phenyl, naphthyl, pyridyl, pyrimidyl, pyridylium, pyrimidylium, triazinyl, each aromatic core being substituted by $C_1$-$C_8$alkyl, halogen, amino, phenyl, $C_1$-$C_4$alkylphenyl, or benzyl;
$R'_4$ is as defined for $R_4$; or is H;
$R_7$ is $C_6$-$C_{18}$alkylene;
Z is halogen or $N^+R_8R_9R_{10}$;
$R_8$, $R_9$ and $R_{10}$ independently are selected from the group consisting of $C_1$-$C_{20}$alkyl, $C_7$-$C_{20}$ phenylalkyl, and $C_4$-$C_{12}$cycloalkyl; or all of $R_8$, $R_9$ and $R_{10}$ are linked together to form, together with the nitrogen atom they are bonding to, a substituted or unsubstituted N-heterocyclic ring system of 4-7 carbon atoms.

5. The composition according to claim 1, where
$R_1$ and $R'_1$ independently are $C_1$-$C_4$alkyl,
$R_2$ and $R_3$ independently are $C_2$-$C_{12}$alkylene;
X is O or $N(COR_5)$ and Y is $OCOR_5$ or $NHCOR_5$; $R_7$ is $C_6$-$C_{18}$alkylene; Z is halogen or $N^+R_8R_9R_{10}$, $R_8$, and $R_9$ are independently $C_1$-$C_4$alkyl; and $R_{10}$ is selected from the group consisting of $C_2$-$C_{18}$alkyl, $C_7$-$C_{20}$phenylalkyl, and $C_5$-$C_{12}$cycloalkyl; or all of $R_8$, $R_9$ and $R_{10}$ are linked together to form, together with the nitrogen atom to form an N-heterocyclic aromatic ring of 4-7 carbon atoms;
or where X is $NR_4$ and Y is $NHR_4$, where $R_4$ is phenyl, pyridyl, pyrimidyl, triazinyl; or $C_1$-$C_4$alkyl substituted by phenyl, pyridyl, pyrimidyl, triazinyl; or is phenyl, pyridyl, pyrimidyl, triazinyl, each of which is substituted by $C_1$-$C_4$alkyl, halogen, phenyl, $C_1$-$C_4$alkylphenyl, benzyl; or is $C_1$-$C_4$alkyl, which is substituted by phenyl, pyridyl, pyrimidyl, triazinyl, each aromatic core being substituted by $C_1$-$C_4$alkyl, halogen, phenyl, $C_1$-$C_4$alkylphenyl, or benzyl.

6. The composition according to claim 1, where
$R_1$ and $R'_1$ independently are $C_1$-$C_4$alkyl,
$R_2$ and $R_3$ independently are $C_2$-$C_{12}$alkylene;
X is O or $N(COR_5)$ and Y is $OCOR_5$ or $NHCOR_5$, where $R_7$ is $C_6$-$C_{18}$alkylene; Z is $N^+R_8R_9R_{10}$, where $R_8$, and $R_9$ independently are $C_1$-$C_4$alkyl and $R_{10}$ is selected from the group consisting of $C_8$-$C_{14}$alkyl, $C_7$-$C_{14}$phenylalkyl, and cyclohexyl; or all of $R_8$, $R_9$ and $R_{10}$ are linked together to form a group of the formula

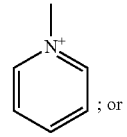

; or

X is $NR_4$ and Y is $NHR_4$, where $R_4$ is phenyl, pyrimidyl; or $C_1$-$C_4$alkyl substituted by phenyl, pyrimidyl;
or is phenyl or pyrimidyl each of which is substituted by $C_1$-$C_4$alkyl and/or phenyl.

7. The composition according to claim 1 wherein component (B) is present in an amount from 0.01 to about 40%, relative to the weight of the carrier.

8. The composition according to claim 1, wherein component (A) is selected from the group consisting of solid inorganic carriers, aqueous liquid carriers, aqueous semisolid carriers, organic liquid carriers, organic semisolid carriers, and solid organic carriers.

9. The composition according to claim 1 wherein said composition is a component of a further composition or article said further composition or article is selected from the group consisting of antifouling composition, coating composition or material, paint, coating system, cosmetic formulation, home care composition, pharmaceutical composition, laundry detergent, fabric care composition, a natural or synthetic fabric, natural or synthetic fibre, non-woven, molded or blow-molded synthetic polymer article, and synthetic polymer film.

10. The composition according to claim 9 wherein said composition further comprises a further component selected from the group consisting of antioxidants, UV absorbers, benzofuran-2-ones, polyamide stabilizers, metal stearates, nucleating agents, fillers, reinforcing agents, clarifiers, modifiers, acid scavengers, lubricants, emulsifiers, dyes, pigments, dispersants, optical brighteners, flow control agents, flame retardants, antistatic agents, blowing agents, thixotropic agents, adhesion promoters, light stabilizers, curing catalysts, accelerators and inhibitors.

11. Oligo- or polysiloxane compound containing at least 3 Si atoms in the main chain, and wherein at least one thereof is contained in a moiety of the formula I as described in claim 1.

12. Oligo- or polysiloxane compound according to claim 11 comprising from 4 to 3000 Si atoms in the main chain.

13. A method for the inhibition of microbial growth wherein said method comprises applying to an article and/or material an effective amount of one or more oligo- or polysiloxane compounds according to claim 1, mixtures comprising two or more said compounds and/or compositions comprising one or more said compounds, and/or a salt thereof.

14. A method for the antimicrobial protection within or on the surface of an article and/or material, wherein said method comprises applying on, incorporating into, and/or impregnating said article with an oligo- or polysiloxane compound according to claim 1.

15. A method for the inhibition of microbial growth in a medicament, a cosmetic formulation or a pharmaceutical formulation wherein said method comprises applying to said medicament, cosmetic formulation or pharmaceutical formulation an effective amount of one or more oligo- or polysiloxane compounds according to claim 1, mixtures comprising two or more said compounds and/or compositions comprising one or more said compounds, and/or a salt thereof.

* * * * *